Figure 1:
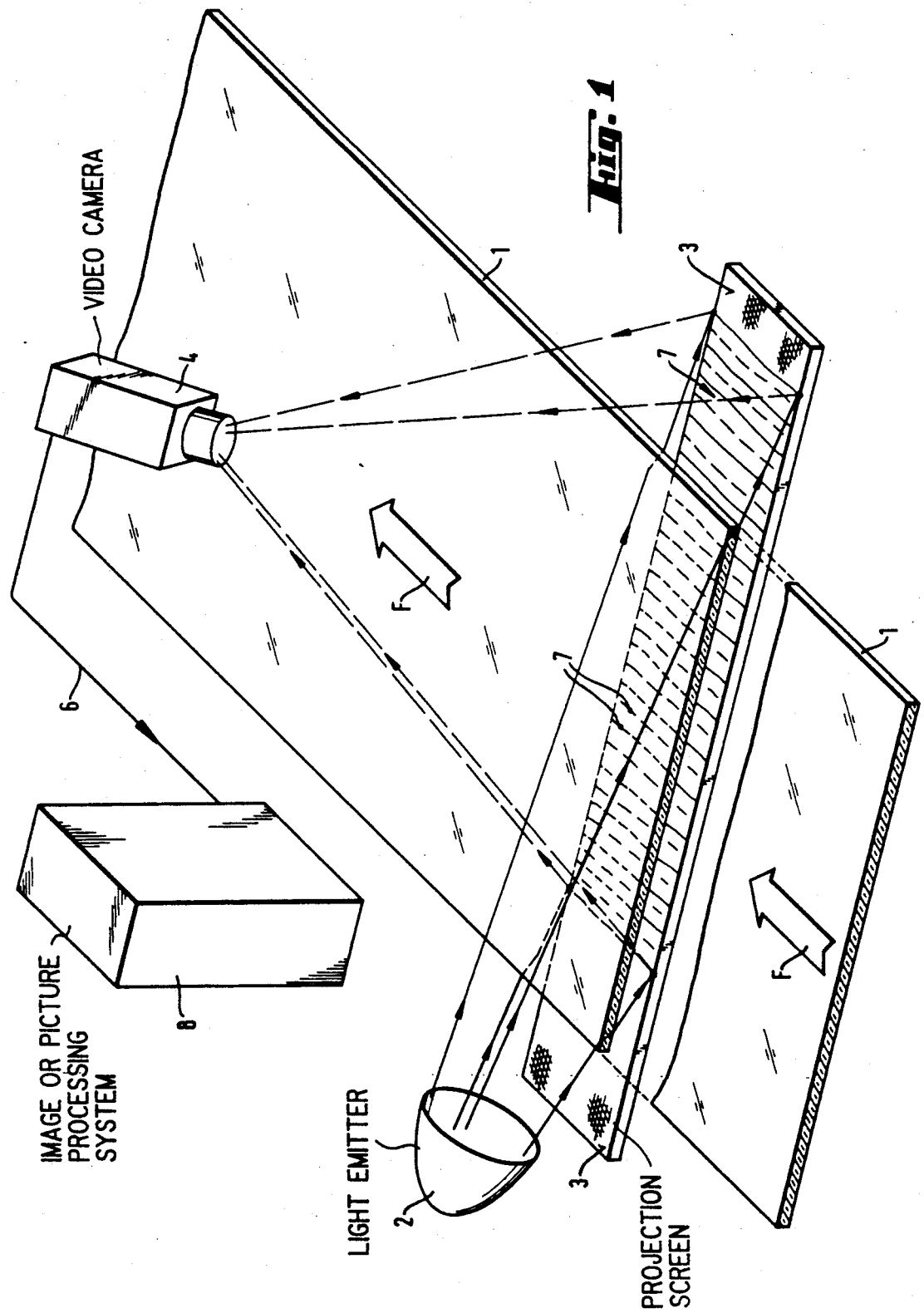

United States Patent [19]

Bongardt et al.

[11] Patent Number: 5,016,099
[45] Date of Patent: May 14, 1991

[54] PROCESS FOR DETERMINING THE OPTICAL QUALITY OF FLAT GLASS OR FLAT GLASS PRODUCTS

[75] Inventors: Wolfgang Bongardt, Aachen; Helmut Gowert, Stolberg; Hans-Josef Winkeler, Aachen; Josef Schneiders, Stolberg, all of Fed. Rep. of Germany

[73] Assignee: Saint-Gobain Vitrage, Courbevoie, France

[21] Appl. No.: 349,692

[22] Filed: May 10, 1989

[30] Foreign Application Priority Data

May 13, 1988 [DE] Fed. Rep. of Germany ....... 3816392

[51] Int. Cl.⁵ ............................................. H04N 7/18
[52] U.S. Cl. ...................................... 358/106; 73/105
[58] Field of Search ................... 358/106, 107; 73/105

[56] References Cited

U.S. PATENT DOCUMENTS

| | | | |
|---|---|---|---|
| 3,877,814 | 4/1975 | Hess et al. | 356/120 |
| 4,647,197 | 3/1987 | Kitaya | 358/106 |
| 4,853,777 | 8/1989 | Hupp | 73/105 |

FOREIGN PATENT DOCUMENTS

| | | |
|---|---|---|
| 0060160 | 5/1985 | European Pat. Off. |
| 2318532 | 11/1973 | Fed. Rep. of Germany. |
| 3021488 | 12/1981 | Fed. Rep. of Germany. |

OTHER PUBLICATIONS

"Surface Roughness Measurement", J. K. Alstad et al., *IBM Technical Disclosure Bulletin*, vol. 25, No. 11B, Apr. 1983, pp. 6009–6010.
Materialpruefung (Material Testing), 21, 1979, No. 5, pp. 153–156.
Messen and Pruefen/Automatik (Measuring and Testing/Automation), Jan./Feb. 1977, pp. 34–41.
Ergebnisse der exakten Naturwissenschaften (Results of the Exact Natural Sciences), vol. 20, Springer-Verlag, Berlin, 1942, pp. 349–365.

*Primary Examiner*—Howard W. Britton
*Attorney, Agent, or Firm*—Oblon, Spivak, McClelland, Maier & Neustadt

[57] ABSTRACT

For determining the optical quality of float glass, at an appropriate point on the production line a silhouette is produced on the projection screen of the float glass ribbon. The silhouette is detected by a video camera and evaluated by digital image processing. The luminance profile of the silhouette is determined from the video picture. The refractive power profile is calculated from the luminance profile and is digitally and/or graphically represented and evaluated.

21 Claims, 5 Drawing Sheets

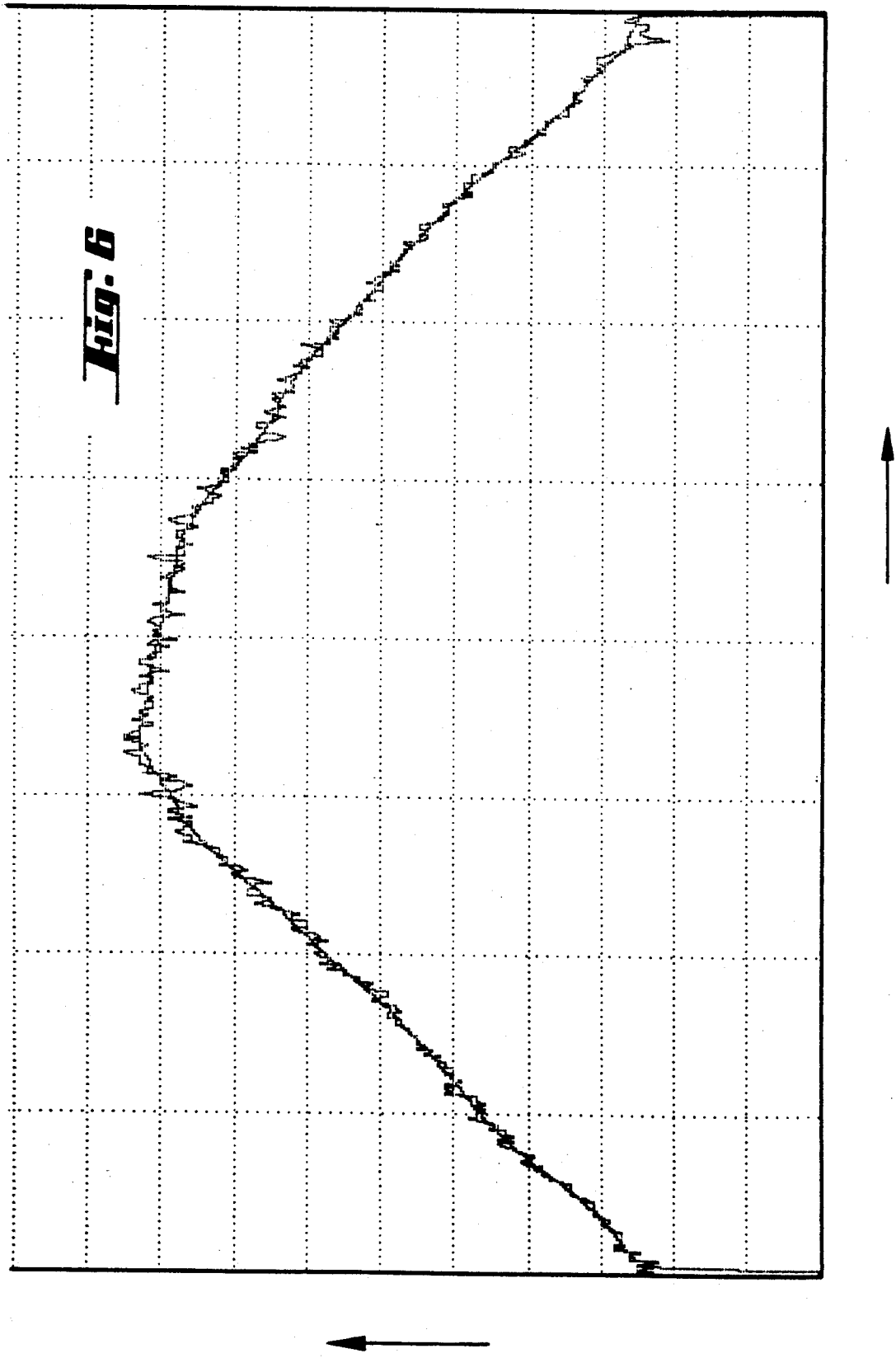

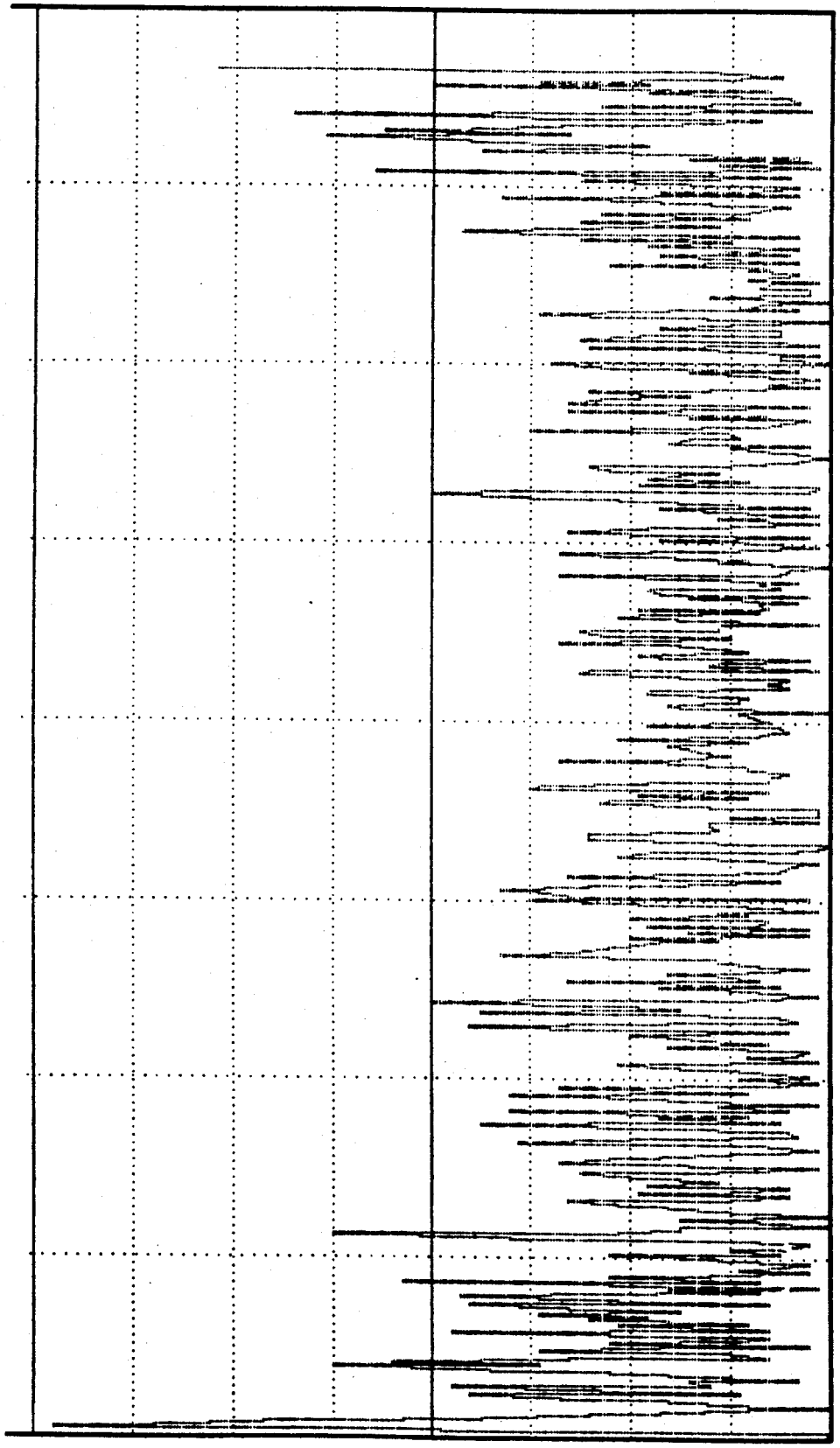

PROCESS FOR DETERMINING THE OPTICAL QUALITY OF FLAT GLASS OR FLAT GLASS PRODUCTS

The invention relates to a process for determining the quality of flat glass and products made from flat glass, particularly float glass and products made from float glass, in which the glass plate is illuminated under an oblique angle of incidence and a silhouette is produced on the projection screen of the illuminated glass plate, said silhouette corresponding to the strip-like areas extending in one direction of the glass plate with the character of convex or concave cylindrical lenses comprises light and dark strips associated therewith.

Flat glass and particularly flat glass produced by the float process, regularly has strip-like surface unevenesses caused by the production process on one or both surfaces extending in the longitudinal direction, i.e. in the pulling direction of the ribbon of glass. The strip-like surface unevenesses characteristic of float glass are also called "float distortions". These surface unevenesses are so minor, that they cannot be detected with mechanical measuring methods. For determining the optical quality of float glass optical control processes are consequently exclusively used.

A known process for evaluating the surface quality of glass plates is the so-called shadow process, in which a visual assessment takes place of the silhouette produced on a projection screen on transmitting light through the glass plate. The unevenesses on the glass plate surfaces act in the manner of converging or diverging lenses and lead to a pattern of light and dark strips on the screen. A quantitative evaluation of the resulting silhouette is not possible with the aid of the known process.

The process for checking the optical quality of float glass described in DE-AS 23 18 532 also makes use of the shadow process, in which the silhouette formed by reflection on a surface of the glass ribbon is observed in order to separately determine the surface unevenesses on both sides of a float glass ribbon. To ensure that a higher proportion of light is reflected on the entrant surface, light polarized linearly to the glass surface is used and is radiated on to the glass plate under angles between 57° and 85°. Reference is admittedly made therein to the possibility of evaluating the silhouette by light measuring instruments and which can in particular comprise a row of photoelectric converters extending transversely over the silhouette, such as photoresistors, phototransistors, etc. However, this process also fails to provide absolute information on the size of the optical defects of the glass ribbon.

In addition, processes are known for the automatic checking of glass products using a digital computer, in which a test pattern consisting of lines or dots is recorded through the test object with a video camera and the distortions of the test pattern caused by defects in the test object are evaluated by digital processing of the video signals (DE-OS 32 37 511 and U.S. Pat. No. 4,647,197). However, this known process also does not permit absolute measurements of the size of dioptric defects in flat glass plates.

For certain uses of glass plates, it is necessary or desirable to be able to measure and indicate the optical quality of the glass plates in absolute values of the refractive power of the dioptric defects. For example, for motor vehicle windshields it is prescribed in the German Road Traffic Authorization Order that in the case of windshields the refractive power value change must be no more thatn ±0.06 diopters. Prior art measuring processes enabling a quantitative measurement of dioptric errors of glass plates to be performed are very complicated and are not suitable for use in production lines.

The problem of the present invention is to provide a process for the determination of the optical quality of flat glass, particularly float glass, which makes it possible to determine the refractive power of the strip-like optical defect or error regions in absolute values and to permit the association of the measured refractive power values with the points on the glass plate corresponding thereto. It must be possible to use this process directly on a production line, in order to more or less continuously inspect the entire float glass production line.

According to the invention this problem is solved by a process of the aforementioned type through the combination of the following features:

the silhouette is determined with a video camera in a narrow measuring field running substantially at right angles to the light and dark strips;

corresponding digitized signals are produced in the video camera or in a series connected digitization stage for the luminance (picture halftone) of each image or picture point;

the difference signal is in each case formed between the digitized signals corresponding to the measured luminance profile and the signals corresponding to the luminance profile of a plane-parallel, defect-free glass plate (basic luminance profile);

the quotient is in each case formed from said different signals and the corresponding signals for the basic luminance; and by multiplying said quotients with a correction factor the absolute values of the refractive powers or values proportional thereto are determined and numerically and/or graphically evaluated.

The invention provides a process making it possible in a simple manner and without complicated optical means to carry out a quantitative determination of the refractive powers in the float glass solely from the silhouette. The means required in the vicinity of the glass plate to be tested merely consist of the lighting unit, a projection scren and one or more video cameras and it is easily possible to install these means directly on a float glass production line. As the evaluation of video picture by the picture processing system can take place in a very short time, e.g. a float glass ribbon moving at a speed of 30 m/min can be tested at 5 cm intervals along a line extending over the entire glass ribbon width with respect to the size of the dioptric errors or defects. Even when high demands are made on the accuracy of the measured values the measurement can take place at 50 cm intervals at the same float glass ribbon speed in the case of a correspondingly sophisticated evaluation of the test or measured signals. This means that in this way a relatively continuous monitoring of the optical quality of a float glass ribbon is possible directly on the production line.

The invention evaluation process makes it possible to evaluate silhouettes produced after irradiation of the glass plate, in which the dioptric errors are caused by the cooperation of the deformation on both glass plate surfaces and also those silhoutete which are essentially produced by the reflection of the light on one or both surfaces.

The basic luminance profile for the formation of the different signal between the signals corresponding to the measured luminance profile and the signals corresponding to the basic luminance profile is, according to a preferred embodiment of the invention, determined directly from the digitized signals corresponding to the measured luminance profile of the silhouette in the measuring field by low-pass filtering. The digitized signals corresponding to the luminance profile can be both measured unprocessed signals and measured and subsequently prefiltered signals. Low-pass filtering filters out the luminance changes occuring as a result of the dioptric defects in the glass plate.

Another possibility for the direct determination of the difference signal necessary for the further calculation between the signals corresponding to the measured luminance profile and the signals corresponding to the basic luminance profile consists of a high-pass filtering of the signals corresponding to the measured luminance profile or the prefiltered signals. In the case of this high-pass filtering the lower threshold frequency of the high-pass filter corresponds to the upper threshold frequency of the low-pass filter used in the previously described case for determining the basic luminance.

According to the invention the quotient is in each case formed from the difference signals and the signals correspoinding to the basic luminance. The signals for the basic luminance required for this quotient formation can in turn be determined in different ways. Thus, for example, it is possible to determine the signals for the basic luminance profile in that the latter is measured beforehand under the same illumination or lighting conditions as for the actual measurement on an optically defect-free, plane-parallel glass plate of the same thickness whilst shielding against interfering extraneous light and then storing the measured signals. Appropriately use is made of a defect-free, plane-parallel glass plate, in which the surfaces have been ground in plane-parallel manner. However, the basic luminance profile can also be previously determined on a normal, i.e. defective glass plate, followed by the filtering out by low-pass filtering of the luminance changes attributable to the optical defect and then the thus determined basic luminance profile is stored. Here again, when measuring the basic luminance profile on the one hand the same lighting conditions must exist as during the subsequent measurement of the actual luminance profiles and on the other hand shielding against interfering extraneous light must take place.

In a particularly appropriate development of the inventive process the determination of the signals for the basic luminance required for quotient formation takes place from the measured luminance profile, namely by symmetrical low-pass filtering of the signals corresponding to the directly measured or prefiltered, actual luminance profile. Thus, in this case quotient formation is based on the basic luminance profile determined from the measured, actual luminance profile.

When processing the digitized signals noise components are filtered out and appropriately in a symmetrical matrix spatial filter with an upper limit for the spatial frequency of at least 1 mm. It is also appropriate to determine the luminance profile along a strip and not along a single line of the video picture, said strip covering a row of lines of the video picture. Representative mean values are then formed by appropriate low-pass filtering from the signals which are juxtaposed at right angles to the picture line direction. The noise components of the picture are hereby further reduced.

When determining the basic luminance for forming the difference signal and/or the quotient, low-pass filtering of the signals corresponding to the measured luminance profile takes place in a symmetrical low-pass filter, whose upper limit for the spatial frequency is set to a suitable value between 1/80 mm and 1/12 mm. (Symmetrical filtering in general means zero-phase-shift-filtering).

The above filtering operations can be carried out singly or together either in a resultant matrix filter in the spatial range, or in a resultant filter in the image range of a two-dimensional linear transformation, such as the 2D Fourier or 2D Walsh transformation, or by interposing one-dimensional linear transformations, such as Fourier or Walsh transformations.

The basic luminance need not be constant over the width of the glass plate, i.e. considered in the longitudinal direction of the measuring field in the above processes and can instead change in random manner provided that said changes are not sudden.

If it is ensured that both the basic luminance and the angle of incidence of the light remain constant over the glass ribbon width, the inventive process can be simplified in that the formation of the difference signal and the formation of the quotient of the difference signal and the basic luminance are performed in a single process stage. As the basic luminance is constant and known, in this special case the refractive power is obtained by subtracting the actual luminance signal from the constant basic luminance and quotient formation also takes place with the aid of the correction factor. It is obviously necesary in this simplified process to shield the complete test system against interfering extraneous light. However, this simplified process does require a spatially constant basic luminance for a constant angle of incidence. However, as it is not easy to obtain these conditions in practice, preference is given to the previously described process, in which the basic luminance and the incidence angle can vary.

The inventive process is obviously not only usable on a float glass line, but can be used in the same way for determining the optical quality of individual glass plates or finished products made from float glass, e.g. finished car windscreens. For determining the optical quality of finished car windscreens, it can be appropriate to test them along two directions at a right angle to one another and to arrange the measuring fields in a grid-like raster. The latter is to be arranged in such a way that the longitudinal extension of the measuring fields is in each case substantially in a direction at right angles to the shadow strips. Optionally, by a preceding fan-shaped arrangement of the measuring fields, it is possible to determine the main direction of the strip-like optical errors, in order to orient the angular position of the grid-like raster.

Further appropriate developments, as well as advantages and details of the inventive process can be gathered from the subclaims and the following description of an embodiment appropriate for the on-line measurement of a float glass line. In the drawings show:

FIG. 1: The apparatus necessary for performing the process in the form of a diagrammatic general drawing.

Figure 2:
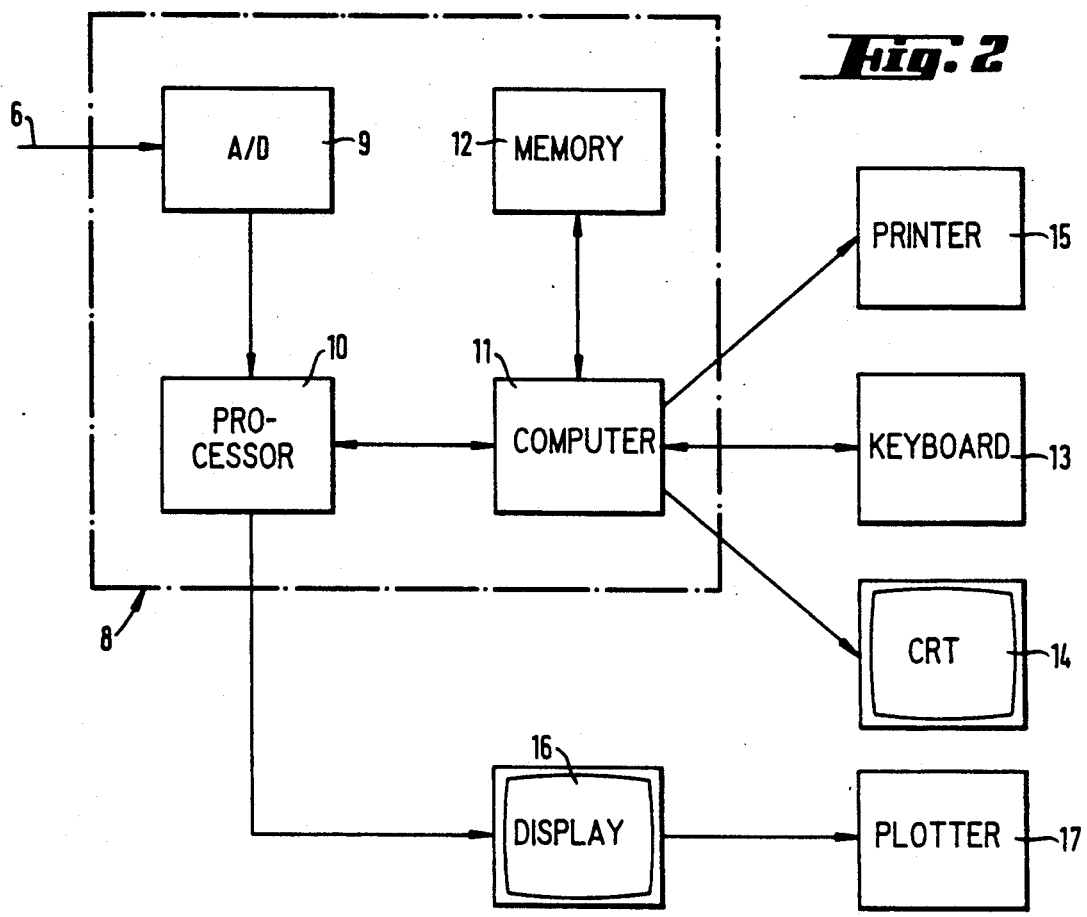

FIG. 2: The essential components necessary for digital image processing in the form of a block diagram.

Figure 3:
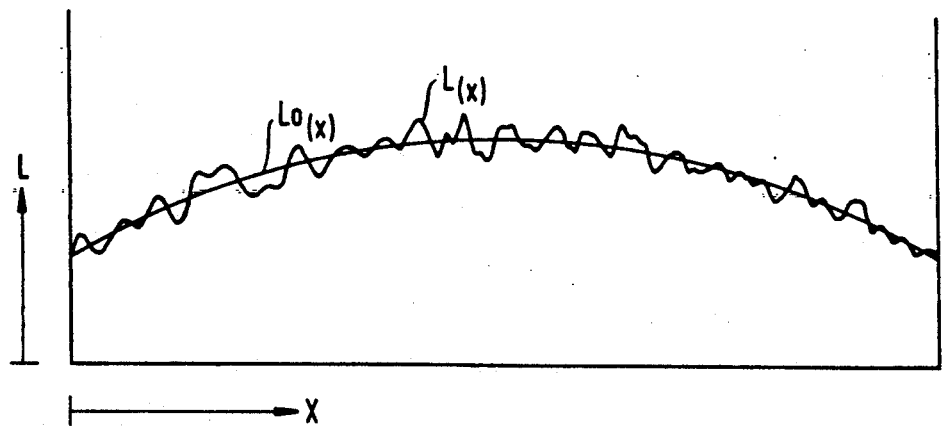

FIG. 3: A graph representing the basic luminance profile and the measured luminance profile of the silhouette.

Figure 4:
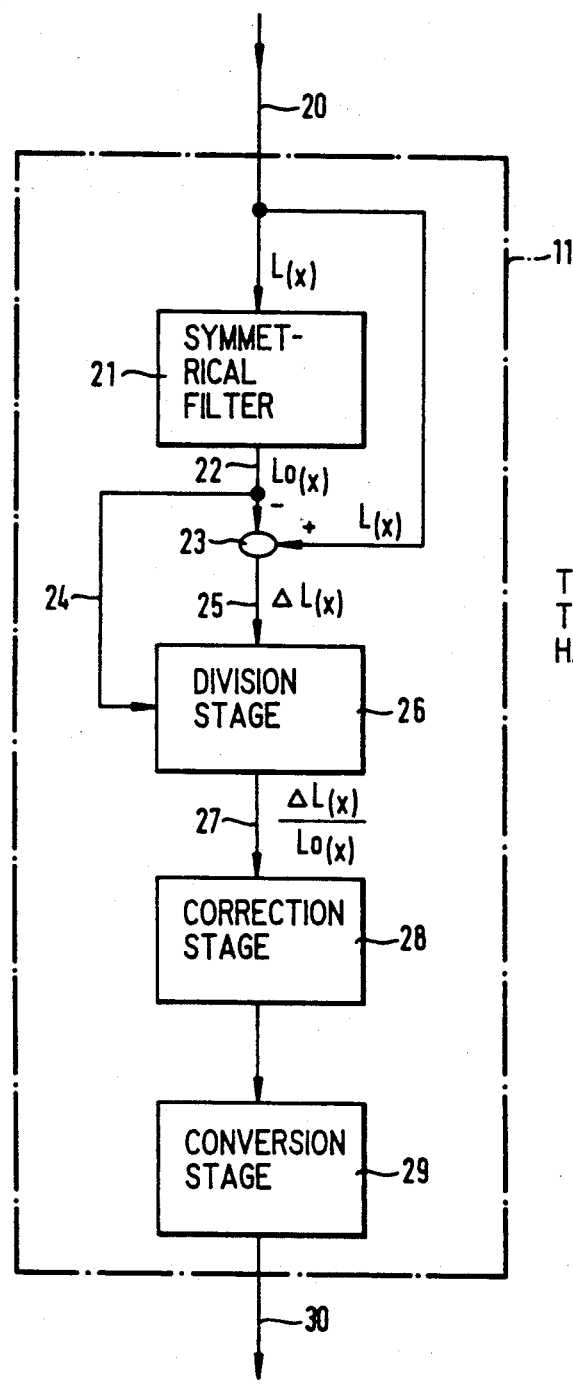

FIG. 4: A block diagram for the circuit for calculating the refractive powers from the digitized signals.

Figure 5:
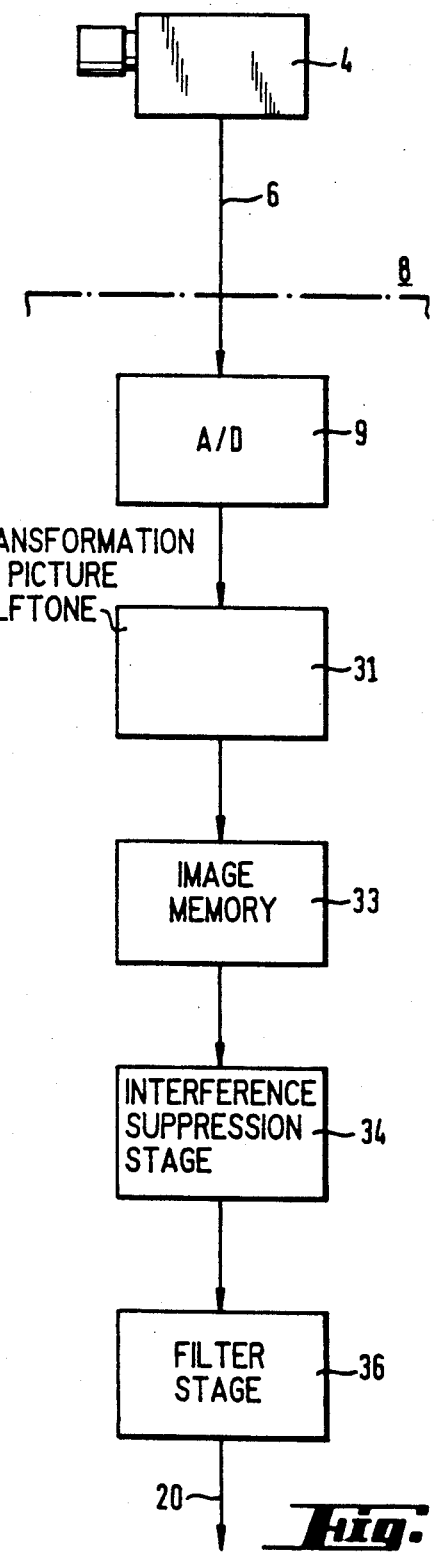

FIG. 5: A block diagram for a circuit for processing the signals supplied by the video camera prior to the actual calculating circuit.

FIG. 6: The print-out of a measured luminance profile and the basic luminance profile determined therefrom.

FIG. 7: The print-out of the refractive power pattern in millidiopters calculated from the values shown in FIG. 6.

As shown in FIG. 1, a continuously produced float glass ribbon 1, here in the form of a ribbon portion, moves at a speed of approximately 10 to 30 m/min, as a function of the glass thickness, in the direction of arrow F towards a not shown cutting station. In the latter glass plates of an approximate length 6 m are separated from the ribbon and stacked. The width of the glass ribbon is more than 3 m.

At an appropriate point within the production line an adequately large area is protected against excessively disturbing daylight or other extraneous light by the arrangement of a cabin with light-impermeable walls and which is not shown so as not to overburden the drawing. A light emitter 2 is positioned laterally of the float glass ribbon 1 within said cabin.

The light emitted by light emitter 2 strikes the glass ribbon under incidence angles between 70° and 80° to the vertical. The oblique illumination under a very large angle of incidence is advantageous, in order to obtain a contrasty silhouette. However, the angle of incidence must not be too large, because then an increasingly high proportion of the light would be reflected on the glass surface and consequently the proportion of the light penetrating the glass ribbon and required for the measurement becomes too small.

A projection screen 3 with a white surface is positioned below glass ribbon 1 in the area illuminated by the light emitter 2. The silhouette 7 caused by the strip-like surface unevenesses of the glass ribbon and which are also referred to as float distortions appear on said projection screen 3 in the form of light and dark strips extending in the longitudinal direction of the glass ribbon. The surface corrugations can be looked upon as convex and concave cylindrical lenses. The concave areas, which act as diverging lenses, appear as dark strips on projection screen 3, whilst the convex areas with the effect of converging lenses appear as light strips. The distance between screen 3 and the glass ribbon is not critical, but must be chosen in such a way that the silhouette plane is definitely upstream of the focus of the lenses.

A video camera 4 is arranged above the glass ribbon 1 upstream or downstream of the projection screen 3 considered in the movement direction of said ribbon. The pictures or images recorded by the video camera 4 are supplied via conductor 6 to an image or picture processing system 8, in which the video picture undergoes digital processing.

The image processing system 8, as is diagrammatically shown in FIG. 2, comprises an analog-digital converter 9, which can optionally already be contained in the video camera, a processor 10, a computer 11 and a mass memory 12. An operating keyboard 13, as well as a CRT terminal 14 and a printer 15 are connected to the computer 11. The digital image processing means also comprises a video display 16 connected to processor 10 and a video plotter 17.

In analog-digital converter 9 the signals for each individual image or picture point, which define its location and its brightness or picture halftone, i.e. its luminance, are converted into corresponding digital signals. In order to be able to describe the luminance with an adequate accuracy using digital signals, the entire brightness area to be detected must be subdivided into an adequately large number of picture halftone stages, which must be at least 64. Good results are obtained if e.g. 128 picture halftone stages are available for describing the luminance.

Processor 10 inter alia has the function of converting the original video picture into a transformed video picture with an improved contrast compared with the original picture using known image processing processors. Commercially available image processing cards can be used for the so-called image processor. Processor 10 contains an image memory, in which is stored the improved contrast video image.

The video image with improved contrast transformed with the aid of processor 10 now forms the basis for the first image processing carried out by computer 11. With the aid of an algorithm developed for this purpose from the luminance information stored in the image memory of the processor 10, computer 11 calculates the refractive power profile of the glass ribbon. To computer 11 is connected a mass memory 12, which is used for storing the programmes and filing the original or improved contrast video images and/or the images calculated therefrom, together with the associated refractive power values.

The development of the algorithm on the basis of which computer 11 carries out the calculation of the refractive power profile from image information present in the image memory of processor 10, takes place by mathematical derivation for the case that the light is transmitted through the glass ribbon and the screen with the silhouette is located on the light exit side at a distance from the ribbon. It has been found that the distance from the screen to the glass ribbon is a constant factor in the calculation and that the refractive power D of the glass plate at a point x can be calculated according to formula $$D_{(x)} = K \frac{\Delta L_{(x)}}{L_{0(x)}}$$

in which the following meanings are used:
D = refractive power in diopters
K = constant
ΔL = difference between measured effective luminance and the basic brightness
Lo = basic brightness measured on the screen with an ideal plane-parallel glass ribbon.

Thus, all that is necessary for calculating the refractive power is to know the path of the basic brightness over the width of the glass ribbon on the one hand and the path of the effective brightness or luminance over the width of the glass ribbon on the other in the form of digital quantities for the individual image points, so as to be able to calculate therefrom the refractive power path, i.e. the refractive power profile.

FIG. 3 shows for the illumination type represented in FIG. 1 the resulting path of the basic brightness $L_{0(x)}$ over the width of the glass ribbon, as well as the path of the effective, i.e. measured brightness or luminance $L_{(x)}$, a diagrammatic representation form being used. The basic brightness $Lo_{(x)}$ rises continuously to the centre of the glass ribbon. The measured luminance $L_{(x)}$ is a curve looping round the basic brightness curve. The basic brightness curve is determined in such a way that it is filtered out of the measured effective luminance profile values with the aid of a symmetrical filter with a low-pass behaviour in the transverse direction to the glass ribbon. The upper threshold frequency of this low-pass filter is adjustable. Good results are obtained if the upper threshold frequency fq of said transverse filter is set to a value between 1/80 mm and 1/12 mm. It has been found that such a calculation of the basic brightness from the measured luminance paths is possible with high reproducibility, provided that there is no disturbing extraneous light and that the thus calculated basic brightness curves are congruent for constant glass thicknesses, even if the calculation takes place over long time intervals.

FIG. 4 illustrates in the form of a block diagram how the processing of the individual image points takes place in computer 11, e.g. when evaluating an individual line of the video picture. The digitized measured value of the actual luminance $L_{(x)}$ of each image point is fed via line 20 to a symmetrical filter 21 with a low-pass behaviour in the transverse direction of the glass ribbon. There is a signal at output 22 of filter 21, which corresponds to the basic brightness $Lo_{(x)}$ of the particular image point. The signal $Lo_{(x)}$ is now supplied in the same way as the signal $L_{(x)}$ branched from line 20 to a subtraction element 23, where the difference $\Delta L_{(x)}$ of these two signals is formed. Signal $Lo_{(x)}$ at output 22 is now supplied via line 24 and difference signal $\Delta L_{(x)}$ via line 25 to a division stage 26, in which the quotient $\Delta L_{(x)}/Lo_{(x)}$ is formed.

The thus found quotient $\Delta L_{(x)}/Lo_{(x)}$ is now supplied across line 27 to a correction stage 28, whose function is to correct the calculated refractive powers, which takes account of the fact that the refractive power is dependent on the angle of incidence. Thus, in the correction stage there is a conversion of the refractive power to the case of vertical light incidence. Correction stage 28 is followed by a conversion stage 29, where the input signal is multiplied by a calibration constant. The latter is empirically determined by comparison with glass plates whose refractive powers are known. The signal is now available in line 30 at the output of conversion stage 29, which directly corresponds to the refractive power of the glass at the point associated with the measured image point. This signal can be supplied to the different units shown in FIG. 2 for further evaluation and/or storage.

The evaluation of a video picture along a single picture line leads to measured values which, due to the noise in the video signal, necessarily are not very accurate. In order to increase the measuring accuracy, it is recommended that a narrow strip of a few juxtaposed picture lines be evaluated, in that the mean value is formed from the luminances of the successive picture points of the picture lines to be evaluated in the longitudinal direction of the glass ribbon. Usable results are obtained if e.g. 4 to 8 successive picture lines are evaluated in this way. The mean value is formed by the series connection of a low-pass filter with an adjustable upper threshold frequency. This manner of image or picture evaluation along a narrow line of only a few picture lines has the advantage that the computer can very rapidly evaluate a video picture, so that this leads to a relatively continuous check or inspection of the float glass ribbon.

When higher demands are made on the accuracy of the measured values, it is recommended that the calculation be based on mean values obtained over strips several centimetres wide. For example, a very high measuring accuracy is obtained on evaluating a strip a few centimetres wide. However, in this case the calculation of the refractive power profile by the computer takes much longer. In order to be able to average the luminance of the image points located in a row in the longitudinal direction of the glass ribbon, i.e. at right angles to the strip to be evaluated, the digitized signals associated with these image points undergo interference suppression with a two-dimensional low-pass spatial filter and are filtered in a suitable longitudinal filter, so that in each case representative values for the luminance along the strip to be evaluated are obtained.

FIG. 5 shows in summary form the method of processing the signal supplied by the video camera 4 prior to the actual calculation process, which takes place in accordance with the method shown in FIG. 4. The signal from video camera 4, on request by the computer is converted into a digital video picture in analog-digital converter 9, in that the analog voltage value corresponding to the actual luminance of each image point is converted into a digital value. To improve the picture contrast the original picture halftone is converted into a transformed picture halftone in a transformation stage 31. In order that the luminance profile is not falsified in the transformation stage, a linear transformation is chosen, which images the picture halftone range of the video signal in the maximum halftone range of the image memory. The thus determined, transformed image, which can appear in place of the original image on video display 16 (FIG. 2), is fed into the image memory 33. Interference suppression of the luminance image is carried in interference suppression stage 34. The latter essentially comprises a two-dimensional symmetrical low-pass filter with an adjustable threshold frequency. The interference suppression stage 34 is followed by a filter stage 36 in which, with the aid of a low-pass filter, is formed the representative mean value for the luminance values in a row in the longitudinal direction of the glass ribbon. The low-pass filter in filter stage 36 is symmetrical. Its upper threshold frequency is adjustable and is e.g. 1/80 mm.

Filtering in interference suppression stage 34 and longitudinal filter stage 36 greatly reduce the statistical noise of the picture to the extent that it is not disturbing during the following calculation. At the output of filter stage 36, the signal is present in line 20, which is further processed with the aid of the computer circuit described relative to FIG. 4 to refractive power values.

The result of the signal processing carried out in the described way can be represented and documented in a random manner. A clear representation, which can be reproduced on the video display and also printed out, is shown in the form of printouts in FIGS. 6 and 7. FIG. 6 shows the effective luminance profile and the basic luminance profile obtained therefrom over the width dimension of the glass ribbon and namely on the basis of those values obtained following interference suppression filtering and length averaging of the measured signals (prefiltering). The vertical spacing between two horizontal division lines corresponds to ten picture halftone units.

The refractive power diagram calculated on the basis of the values reproduced in FIG. 6 is shown in FIG. 7, the calculated absolute amounts of the refractive power values once again being plotted in the same scale over the width of the glass ribbon. The vertical spacing of the horizontal division lines corresponds in each case to a refractive power of 2.5 millidiopters. The position and intensity of dioptric errors above an adjustable alarm threshold can be determined and documented automatically in this way. The data can optionally be transmitted by means of a coupling interface to an automating system in which, on the basis of said data, the glass ribbon can be cut and the glass plates sorted in accordance with the customer's quality requirements.

We claim:

1. A process for determining the optical quality of flat glass, particularly float glass, or products made from flat glass, in which the glass plate is illuminated under an oblique angle of incidence and a silhouette of the illuminated glass plate is produced on a projection screen which, corresponding to the strip-like areas extending in the direction of the glass plate with the character of convex or concave cylindrical lenses comprises light and dark strips associated therewith, characterized by the following features:
   (a) the silhouette is determined with a video camera in a narrow measuring field running substantially at right angles to the light and dark strips;
   (b) corresponding digitized signals are produced in the video camera or in a series connected digitization stage for the luminance (picture halftone) of each image or picture point;
   (c) the difference signal is in each case formed between the digitized signals corresponding to the measured luminance profile and the signals corresponding to the luminance profile of a plane-parallel, defect-free glass plate (basic luminance profile);
   (d) the quotient is in each case formed from said different signals and the corresponding signals for the basic luminance; and
   (e) by multiplying said quotients with a correction factor the absolute values of the refractive powers or values proportional thereto are determined and numerically and/or graphically evaluated.

2. A process according to claim 1, characterized in that the basic luminance profile necessary for forming the difference signal is determined by low-pass filtering from the digitized signals corresponding to the luminance profile of the silhouette in the measuring field.

3. A process according to claim 1 or 2, characterized in in that on forming the quotient from the difference signals and the signal for the basic luminance, the basic luminance profile is used as a basis, which has previously been measured under the same lighting conditions on an optically defect-free, plane-parallel glass plate of the same thickness, with shielding against interfering extraneous light and whose associated signals have been stored.

4. A process according to claim 1 or 2, characterized in that during the formation of the quotient from the difference signals and the signals for the basic luminance, the basic luminance profile is used as a basis, which was determined under the same illumination conditions on a defective glass plate of the same thickness, with shielding against interfering extraneous light following symmetrical low-pass filtering of the digitized signals and whose associated signals were stored.

5. A process according to claim 1 or 2, characterized in that during the formation of the quotient from the difference signals and the associated signals for the basic luminance, the basic luminance profile is used as a basis, which was determined by symmetrical low-pass filtering from the measured luminance profile.

6. A process according to claim 5, characterized in that the digital signals representing the luminance of the individual image or picture points have at least 64 and preferably more than 128 steps.

7. A process according to claim 6, characterized in that noisy signals are filtered in a symmetrical matrix spatial filter with an upper spatial frequency limit of at least 1/13 mm.

8. A process according to claim 7, characterized in that the luminance profile is determined and evaluated along a strip comprising a row of lines of the video picture, representative mean values being formed by filtering from the signals corresponding to the picture points juxtaposed at right angles to the line direction.

9. A process according to claim 8, characterized in that a symmetrical filter with an upper spatial frequency limit of 1/80 mm to 1/12 mm is used as the low-pass filter for determining the basic luminance profiles for the formation of the difference signal and/or for the formation of the quotient from the signals corresponding to the luminance profile.

10. A process according to claim 9, characterized in that the filtering with a resultant matrix filter takes place in the spatial range.

11. A process according to claim 9, characterized in that the filtering with a resultant filter takes place in the picture range of a two-dimensional linear transformation, such as the 2D Fourier or the 2D Walsh transformation.

12. A process according to claim 9, characterized in that filtering is carried out by interposing one-dimensional linear transformations, such as the Fourier or Walsh transformation.

13. A process according to claim 12, characterized in that the calculated value for the refractive power is corrected to the value valid for vertical irradiation, whilst taking account of the incidence angle of the light striking the glass plate.

14. A process according to claim 13, characterized in that evaluation takes place of the silhouette formed on the projection screen located at the side of the plate facing the lighting unit, as a result of the irradiation of the glass plate.

15. A process according to claim 13, characterized in that evaluation takes place of the silhouette formed on the projection screen arranged on the same side as the lighting unit, as a result of reflection on the glass plate.

16. A process according to claim 15, characterized in that for determining the refractive powers of a composite glass plate comprising individual glass plates interconnected by a thermoplastic adhesive layer, the evaluation of the silhouette takes place in at least two directions at an angle to one another.

17. An apparatus for determining the optical quality of flat glass or products made therefrom comprising:
   means for illuminating a glass plate under an oblique angle of incidence;
   a projection screen for receiving the silhouette of the illuminated glass plate which corresponds to strip-like areas extending in the direction of the glass plate with the character of the convex or concave cylindrical lens comprised of light and dark strips associated therewith;

video camera means for determining the silhouette in a narrow measured field running substantially at right angles to the light and dark strips;

digitizing means for digitizing the signals produced by said video camera or for providing a digitized signal of the luminance of each image or picture point;

differental signal measuring means for providing a differental signal between the digitized signals produced by said digitizing means corresponding to the measure luminance profile and digitized signals corresponding to the luminance profile of a plane-parallel defect-free glass plate;

quotient detection means for determining the quotient between said differental signals and the corresponding signals for the basic luminance;

multiplying means for providing a quotient with a correction factor equal to the absolute value of the refractive powers or values proportional thereto.

18. Apparatus according to claim 17, characterized in that the image processing system has a filter stage (34) with a two-dimensional, symmetrical low-pass spatial filter for the interference suppression of the noisy signals.

19. Apparatus according to claims 17 or 18, characterized in that the image processing system has filter stage (36) with a low-pass filter for each image column in the longitudinal direction of the glass ribbon.

20. Apparatus according to claim 19, characterized in that it has a filter state (21) for determining the basic luminance profile from the actual luminance profile supplied by the video camera.

21. Apparatus according to claim 20, characterized by a correction stage (28) connected in series with the division stage (26).

* * * * *